(12) United States Patent
Barberi et al.

(10) Patent No.: US 10,180,484 B2
(45) Date of Patent: Jan. 15, 2019

(54) MRI QUALITY ASSURANCE DEVICE

(71) Applicant: MODUS MEDICAL DEVICES INC., London (CA)

(72) Inventors: Enzo Antonio Barberi, London (CA); David John Munro Miller, London (CA)

(73) Assignee: MODUS MEDICAL DEVICES INC., London, Ontario (CA)

( * ) Notice: Subject to any disclaimer, the term of this patent is extended or adjusted under 35 U.S.C. 154(b) by 181 days.

(21) Appl. No.: 15/405,798

(22) Filed: Jan. 13, 2017

(65) Prior Publication Data
US 2017/0205488 A1 Jul. 20, 2017

Related U.S. Application Data

(60) Provisional application No. 62/278,595, filed on Jan. 14, 2016.

(51) Int. Cl.
*G01R 33/58* (2006.01)

(52) U.S. Cl.
CPC .................................. *G01R 33/58* (2013.01)

(58) Field of Classification Search
CPC ...................................................... G01R 33/58
See application file for complete search history.

(56) References Cited

U.S. PATENT DOCUMENTS

| 4,769,602 A * | 9/1988 | Vinegar | G01R 33/4828 324/303 |
| 2015/0114076 A1* | 4/2015 | Bourne | A61N 5/1075 73/1.01 |

\* cited by examiner

*Primary Examiner* — Rodney Bonnette

(57) ABSTRACT

A MRI quality assurance device, according to the present invention, has a housing made of a rigid MRI invisible material containing one or more sealed reservoirs containing a fluid MRI signal producing material. Each sealed reservoir has a first volume portion and a second variable volume portion in fluid communication therewith.

16 Claims, 4 Drawing Sheets

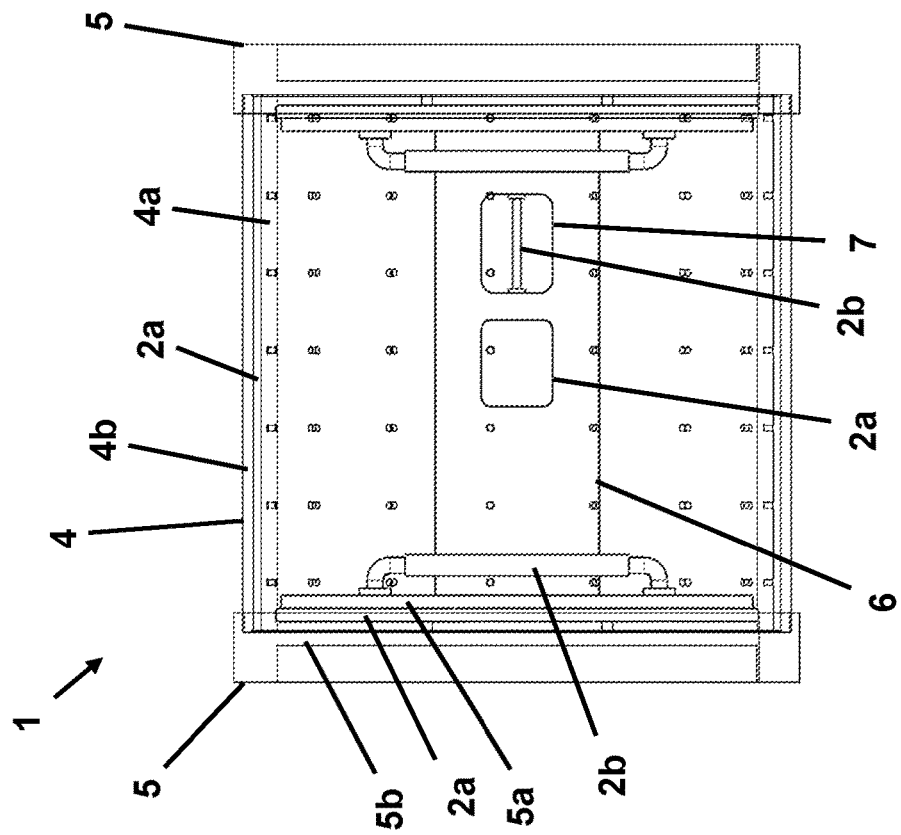
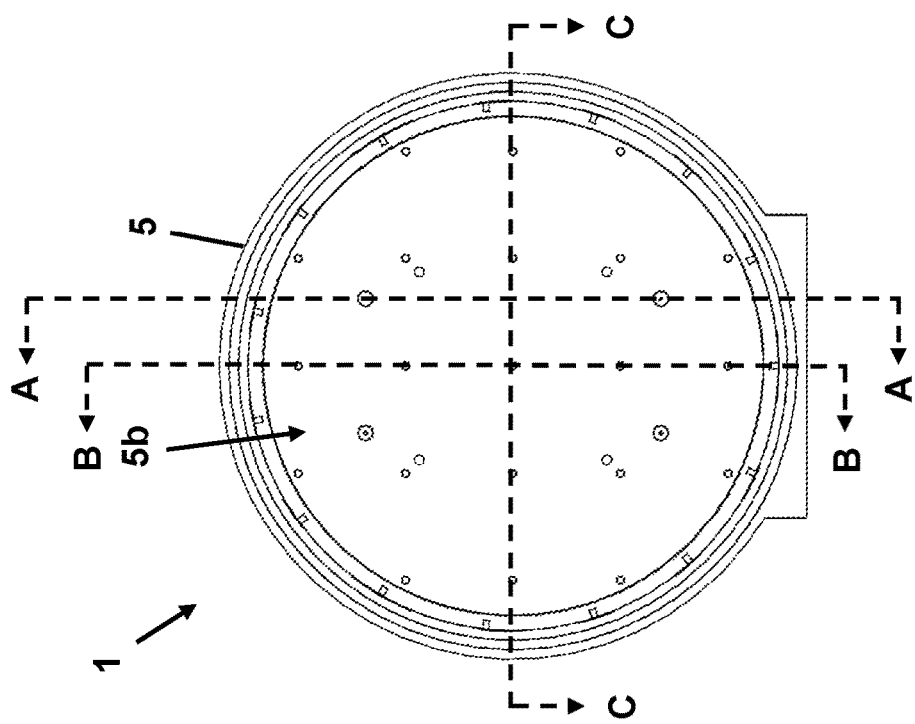
FIG. 3
FIG. 2

MRI QUALITY ASSURANCE DEVICE

FIELD OF THE INVENTION

The present invention relates to quality assurance devices for magnetic resonance imaging (MRI) apparatuses, in particular, to MRI quality assurance devices that compensate for variations in temperature or pressure.

BACKGROUND

Magnetic resonance imaging (MRI) is a well-established diagnostic imaging technique that is useful in many applications, due to its capacity to produce superior soft tissue contrast compared to other diagnostic imaging techniques. MRI is also suitable for use with a wide variety of contrast mechanisms, such as T1, T2, proton density, diffusion tensor imaging, or diffusion weighted imaging, that can reveal both subtle and dramatic anatomical, functional, and pathological details with higher sensitivity and specificity than other imaging techniques.

Recently, MRI is being employed in image guided applications, such as radiation therapy. For example, in image guided radiation therapy, the ability to visualize active tumours and real-time radiation dose distributions is expected to improve targeting of radiation doses to tumour regions and reduce radiation exposure to surrounding healthy tissue. This is expected to result in more efficient treatments and higher survival rates in patients undergoing radiation therapy. Further, in some cases, image guided radiation therapy is the only viable treatment for certain types of cancer.

In image guided applications, geometrical accuracy of the MRI equipment is considerably more important than in diagnostic imaging applications, where modest image distortion does not affect diagnostic outcomes. Image guided applications typically require accuracy, from the MRI equipment, at the millimeter level. By contrast, diagnostic imaging applications can generally tolerate image distortions at the centimeter level.

Quality assurance devices, called MRI geometric distortion phantoms, are used to assess the level of geometric distortion in MRI systems. Geometric distortion may be caused by system imperfections in MRI equipment components, such as the gradient coils or the main B0 magnetic field coils. MRI geometric distortion phantoms, or MRI phantoms, may be used for quality assurance purposes, such as tracking system performance over time, or they may be used by OEM vendors for testing purposes, such as quantifying errors in the image geometry.

MRI phantoms have a known 2D or 3D geometry and contain a MRI signal producing material within a MRI invisible container. Typically, the MRI signal producing material is a liquid and the MRI invisible material is a plastic. The container may also contain either intersecting grid structures of known dimensions or fiducial markers distributed in known positions. The MRI signal producing material and/or other markers are then detected using the MRI system and the resulting image is compared against the known geometry of the MRI phantom to calculate image distortion in the MRI system.

Geometric accuracy of MRI phantoms can be compromised by pressure changes caused by the difference in volume thermal coefficient of expansion of the materials used to construct and fill the MRI phantom. Based on typical values for the volume thermal coefficient of expansion for commonly used materials (mineral oil and acrylic), the change in pressure per degree Celsius ($\Delta P/°$ C.) is about 60 kPa/° C. This is a significant increase in the internal pressure of a sealed vessel, such as a MRI phantom, and can result in geometrical distortion to the MRI phantom itself, thereby affecting the accuracy of the MRI phantom in measuring geometrical distortion of MRI equipment. In addition, the increase in pressure may result in liquid rupturing from the MRI phantom if the MRI phantom is subjected to a wide fluctuation in temperature and/or ambient pressure, such as during shipping.

Accordingly, there is a need for a MRI phantom that is capable of maintaining its structural integrity and geometrical accuracy when subjected to fluctuations in temperature and/or pressure.

SUMMARY OF THE INVENTION

A MRI quality assurance device, according to the present invention, has a housing made of a rigid MRI invisible material containing one or more sealed reservoirs containing a fluid MRI signal producing material. Each sealed reservoir has a first volume portion and a second variable volume portion in fluid communication therewith. The second variable volume portion varies in response to changes in volume of the fluid MRI signal producing material.

According to another aspect of the present invention, an imaging quality assurance device has a housing made of a rigid material containing one or more sealed reservoirs containing a fluid material. Each sealed reservoir has a first volume portion and a second variable volume portion in fluid communication therewith. The second variable volume portion varies in response to changes in volume of the fluid material.

BRIEF DESCRIPTION OF THE DRAWINGS

In order that the invention may be more clearly understood, a preferred embodiment thereof will now be described in detail by way of example, with reference to the accompanying drawings, in which:

FIG. 2 is an end view of the MRI quality assurance device.

FIG. 3 is a side view of the MRI quality assurance device.

DESCRIPTION OF THE PREFERRED EMBODIMENT

A MRI quality assurance device, or a MRI phantom, according to the present invention, is container made of a rigid MRI invisible material with a known 2D or 3D geometry, containing one or more sealed reservoirs containing a fluid MRI signal producing material. Each sealed reservoir has a first volume portion and a second variable volume portion to accommodate fluctuations in volume of the fluid within the sealed reservoir, due to variations in temperature and/or pressure.

As shown in FIGS. 1-7, the MRI phantom has a housing 1 and one or more sealed reservoirs 2, with a first volume portion 2a and a second variable volume portion 2b. The two materials are susceptibility matched to one another to minimize susceptibility gradient induced distortion at the boundary between the different materials. Preferably, the MRI phantom is a boundary-type phantom, such as a Quasar™ MRID 3D Phantom, where the MRI signal producing material is mineral oil, and the MRI invisible material is acrylic. Alternatively, the device of the present invention may be applied to other fluid-filled quality assurance devices for MRI or other imaging modalities.

Figure 1:
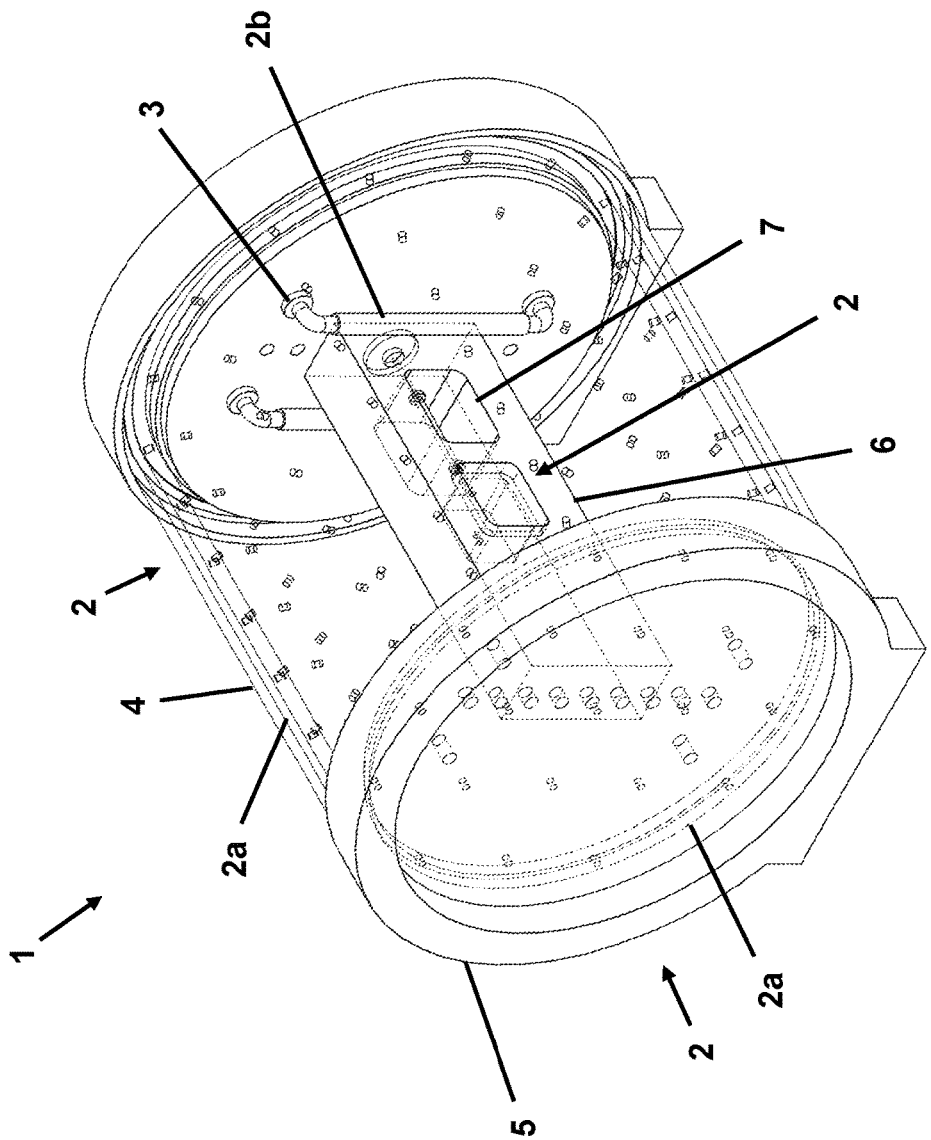
FIG. 1 is a perspective view of a MRI quality assurance device, according to the present invention.

As shown in FIGS. 1-3, the housing 1 is made up of a cylindrical shell 4 and two end plates 5, which are attached on either end of the cylindrical shell 4. The cylindrical shell 4 and end plates 5 have inner and outer walls 4a and 4b, and 5a and 5b, respectively. Therebetween, the cylindrical shell 4 and end plates 5 each contain the first volume portion 2a of a sealed reservoir 2. Preferably, the cylindrical shell 4 and one of the end plates 5 contain one continuous sealed reservoir 2, while the other end plate 5 contains a separate sealed reservoir 2. The first volume portions 2a of the sealed reservoirs 2 are non-expandable chambers with substantially fixed volume defined by the distance between the inner and outer walls 4a and 4b, and 5a and 5b. Some small changes in the dimensions of the inner and outer walls 4a and 4b, and 5a and 5b may result from variations in temperature, but these changes alone do not substantially affect the volume of the first volume portions 2a. The sealed reservoirs 2 are generally the same shape and size as the cylindrical shell 4 and end plates 5.

The MRI phantom may also have a centre rod 6, which also contains a sealed reservoir 2. The centre rod 6 is located centrally within the cylindrical shell 4 and extends between the two end plates 5. The sealed reservoir 2 contained within the centre rod 6 is located centrally within the cylindrical shell 4 and between the two end plates 5, and is significantly smaller than the centre rod 6. Alternatively, the sealed reservoir 2 may be located off-centre in either or both directions and may have an internal volume closer to the size of the centre rod 6.

Figure 4:
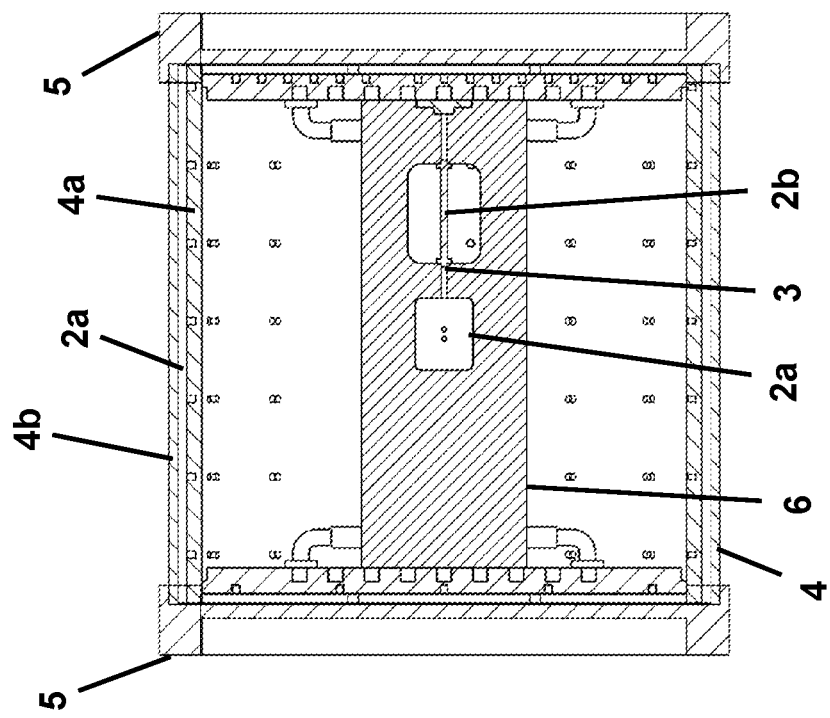
FIG. 4 is a side sectional view of the MRI quality assurance device, along the lines A-A.
Figure 5:
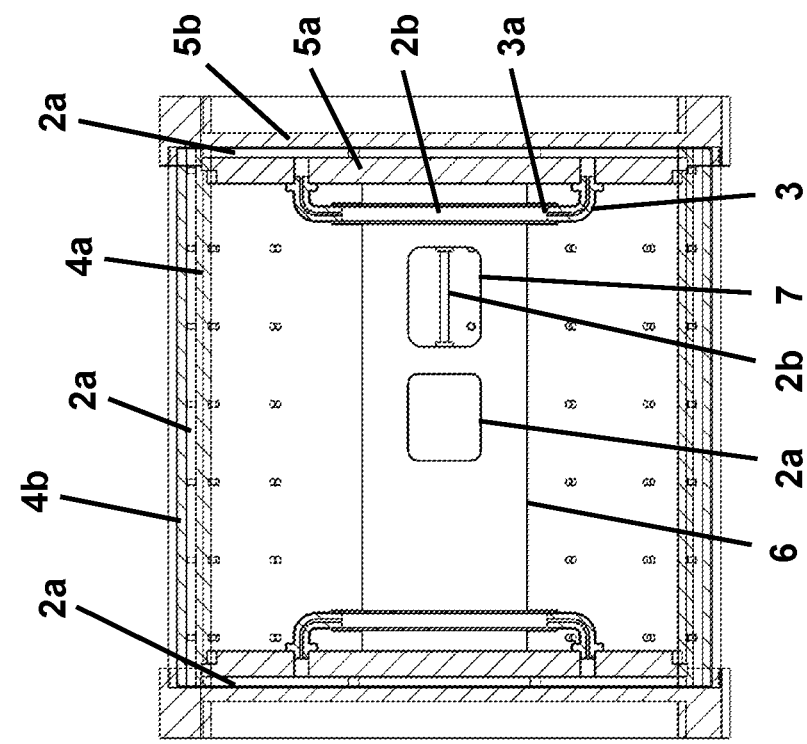
FIG. 5 is another side sectional view of the MRI quality assurance device, along the lines B-B.
Figure 7:
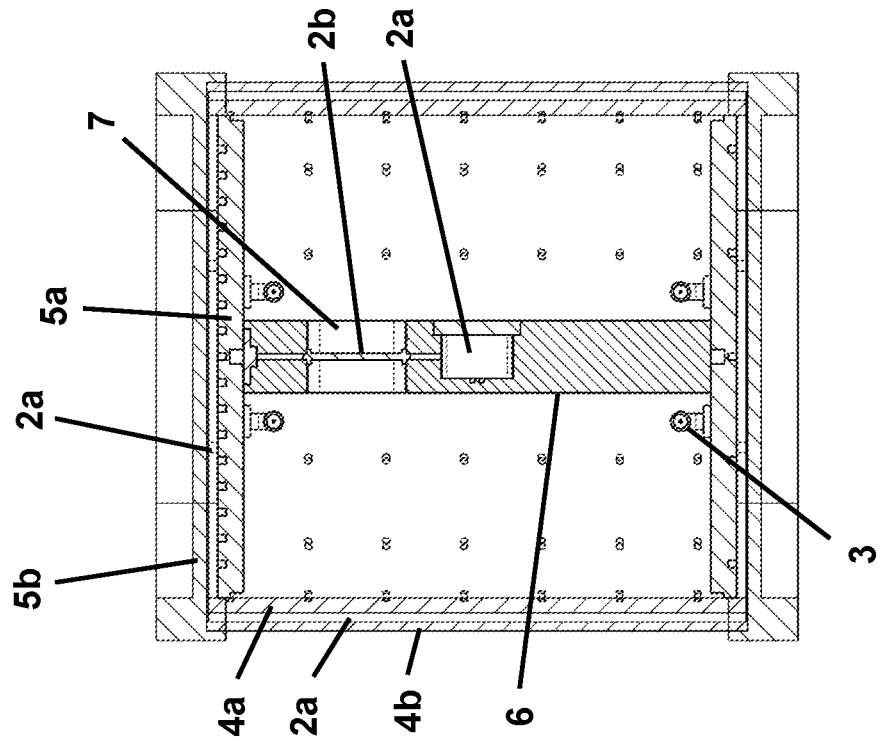
FIG. 7 is a top sectional view of the MRI quality assurance device, along the lines C-C.
Figure 6:
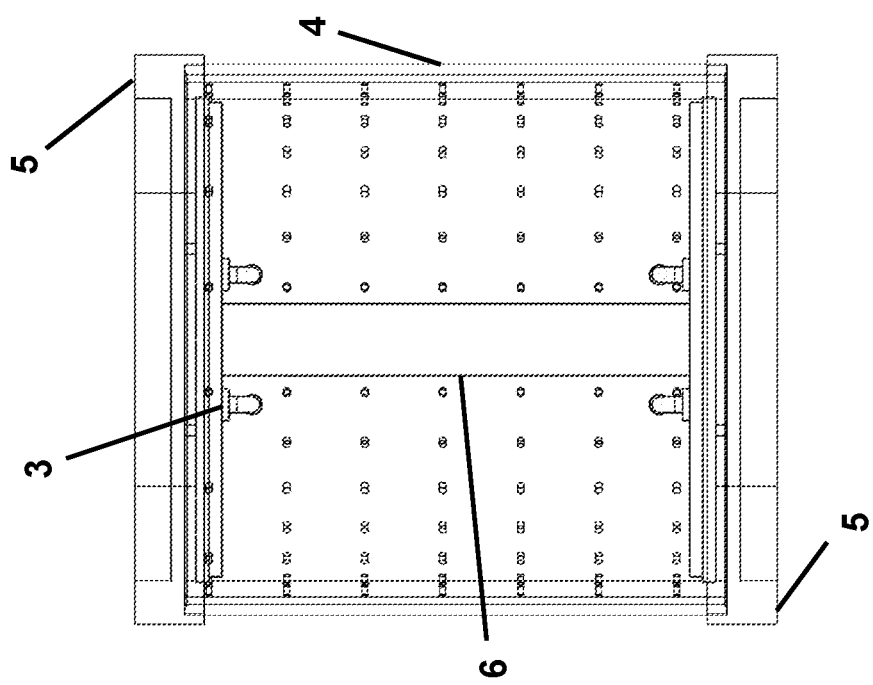
FIG. 6 is a top view of the MRI quality assurance device.

Each sealed reservoir 2 has at least one second variable volume portion 2b, or expandable chamber, to accommodate fluctuations in volume of the liquid within the sealed reservoir 2. As shown in FIGS. 4 and 5, the first volume portion of each sealed reservoir 2 is in fluid communication with its corresponding second variable volume portion(s) 2b, such that the fluid filling the internal volume of the sealed reservoir 2 may flow freely therebetween. Preferably, the second variable volume portions 2b are made of an elastic MRI invisible material, such as a flexible rubber tube, and are coupled to the first volume portions 2a by way of MRI invisible fittings, such as rigid plastic couplers 3 with barbed fittings 3a for receiving an open end of the flexible rubber tube.

As shown in FIG. 4, the second variable volume portions 2b coupled with the corresponding first volume portions 2a of the sealed reservoir 2 contained in the end plates 5 are attached to the inner walls 5a of each end plate 5. Preferably, two separate second variable volume portions 2b are coupled with each the first volume portion 2a with one end of the coupler 3 connected with the first volume portion 2a through the inner wall 5a. The other end of the coupler 3 has a barbed fitting 3a onto which an end of the flexible rubber hose of the second variable volume portion 2b is received and clamped. The fluid filling the sealed reservoir 2 is thereby permitted to flow from first volume portion 2a, through the coupler 3, and into the second variable volume portion 2b and vice-versa.

Where the cylindrical shell 4 contains its own separate sealed reservoir 2, the second variable volume portion(s) 2b coupled with the first volume portion 2a of the cylindrical shell 4 are attached to the inner wall 4a in the same say as the inner wall 5a. The second variable volume portion 2b of the sealed reservoir 2 of the centre rod 6 is located within a recess 7 in the centre rod 6 adjacent the first volume portion 2a and coupled thereto in the same way.

The MRI phantom, according to the present invention, is thereby able to accommodate temperature-induced pressure changes caused by the unavoidable mismatch in thermal coefficient of expansion between the MRI signal producing material filling the sealed reservoirs 2, which is a fluid, such as mineral oil, and the MRI invisible material of the housing 1, which is a solid, such as acrylic. This permits the MRI phantom to maintain the geometric accuracy of the housing 1 and first volume portions 2a over a range of temperatures. This also assist the MRI phantom in minimize the risk of rupture/leaks in the sealed reservoirs 2 when the MRI phantom is subjected to fluctuations in temperature and/or pressure, such as during shipping.

A number of embodiments of the present invention have been described and shown in the accompanying drawings. Nonetheless, the embodiments are described herein illustratively and are not meant to limit the scope of the invention, as claimed. Variations of the foregoing embodiments will be evident to a person of ordinary skill and are intended by the inventor to be encompassed by the following claims.

What is claimed is:

1. A MRI quality assurance device, comprising a housing made of a rigid MRI invisible material containing one or more sealed reservoirs containing a fluid MRI signal producing material, wherein each of the one or more sealed reservoirs has a first volume portion and a second variable volume portion in fluid communication therewith, and wherein the second variable volume portion varies in response to changes in volume of the fluid MRI signal producing material.

2. The MRI quality assurance device of claim 1, wherein the first volume portion is a non-expandable chamber in the housing and the second variable volume portion is an expandable chamber in the housing.

3. The MRI quality assurance device of claim 2, wherein the housing comprises a cylindrical shell and two end plates each having hollow walls defining one or more non-expandable chambers in fluid communication with one or more expandable chambers.

4. The MRI quality assurance device of claim 3, wherein the expandable chamber is a rubber tube.

5. The MRI quality assurance device of claim 1, wherein the first volume portion is one or more non-expandable chambers in the housing.

6. The MRI quality assurance device of claim 5, wherein the second variable volume portion is one or more expandable chambers in the housing.

7. The MRI quality assurance device of claim 1, wherein the MRI invisible material and MRI signal producing material are susceptibility matched to minimize susceptibility gradient induced distortion.

8. The MRI quality assurance device of claim 7, wherein the MRI invisible material is acrylic and the MRI signal producing material is mineral oil.

9. An imaging quality assurance device, comprising a housing made of a rigid material containing one or more sealed reservoirs containing a fluid material, wherein each of the one or more sealed reservoirs has a first volume portion and a second variable volume portion in fluid communication therewith, and wherein the second variable volume portion varies in response to changes in volume of the fluid material.

10. The imaging quality assurance device of claim 9, wherein the first volume portion is a non-expandable chamber in the housing and the second variable volume portion is an expandable chamber in the housing.

11. The imaging quality assurance device of claim 10, wherein the housing comprises a cylindrical shell and two end plates each having hollow walls defining one or more non-expandable chambers in fluid communication with one or more expandable chambers.

12. The imaging quality assurance device of claim 11, wherein the expandable chamber is a rubber tube.

13. The imaging quality assurance device of claim 9, wherein the first volume portion is one or more non-expandable chambers in the housing.

14. The imaging quality assurance device of claim 13, wherein the second variable volume portion is one or more expandable chambers in the housing.

15. The imaging quality assurance device of claim 9, wherein the rigid material and fluid material are susceptibility matched to minimize susceptibility gradient induced distortion.

16. The imaging quality assurance device of claim 15, wherein the rigid material is acrylic and the fluid producing material is mineral oil.

* * * * *